United States Patent
Wakefield et al.

(10) Patent No.: US 8,301,259 B2
(45) Date of Patent: *Oct. 30, 2012

(54) USING A GENETIC ALGORITHM TO FIT A COCHLEAR IMPLANT SYSTEM TO A PATIENT

(75) Inventors: Gregory Wakefield, Ann Arbor, MI (US); Chris Van Den Hobert, Aurora, CO (US); Aaron Parkinson, Parker, CO (US); Wendy Parkinson, Parker, CO (US); Sean Lineaweaver, Parker, CO (US); Jim Patrick, Roseville (AU); John Parker, Roseville (AU)

(73) Assignee: Cochlear Limited, Marquarie University, NSW (AU)

( * ) Notice: Subject to any disclaimer, the term of this patent is extended or adjusted under 35 U.S.C. 154(b) by 634 days.

This patent is subject to a terminal disclaimer.

(21) Appl. No.: 10/963,594

(22) Filed: Oct. 14, 2004

(65) Prior Publication Data
US 2005/0107845 A1 May 19, 2005

Related U.S. Application Data

(63) Continuation-in-part of application No. 10/385,880, filed on Mar. 11, 2003, now Pat. No. 6,879,860, and a continuation-in-part of application No. PCT/US2004/007400, filed on Mar. 11, 2004.

(51) Int. Cl.
*A61N 1/00* (2006.01)
(52) U.S. Cl. .......................................................... 607/57
(58) Field of Classification Search .................... 607/57, 607/56, 55, 59; 600/559
See application file for complete search history.

(56) References Cited

U.S. PATENT DOCUMENTS

| | | | |
|---|---|---|---|
| 4,532,930 A * | 8/1985 | Crosby et al. | 607/57 |
| 4,953,112 A | 8/1990 | Widin et al. | |
| 5,095,904 A | 3/1992 | Seligman et al. | |
| 5,277,694 A * | 1/1994 | Leysieffer et al. | 600/25 |
| 5,626,629 A | 5/1997 | Faltys et al. | |
| 6,157,861 A | 12/2000 | Faltys et al. | |
| 6,697,674 B2 * | 2/2004 | Leysieffer | 607/57 |

(Continued)

FOREIGN PATENT DOCUMENTS

JP 09-325773 12/1997

(Continued)

OTHER PUBLICATIONS

Forrest, Stephanie, "Genetic Algorithms: Principles of Natural Selection Applied to Computation," Science, Aug. 13, 1993, vol. 261 (5123), pp. 872-878.

(Continued)

*Primary Examiner* — Scott M. Getzow
(74) *Attorney, Agent, or Firm* — Kilpatrick Townsend & Stockton LLP

(57) ABSTRACT

Apparatus and method for at least partially fitting a cochlear implant system to a patient is described, comprising: executing a genetic algorithm to select values for a subset of one or more parameters selected from a plurality of parameters for which values are to be selected to fit the implant, wherein said genetic algorithm is operable to generate one or more successive generations of values for said parameter subset; and determining, based on patient feedback, said values of said values for said parameter subset in each of said one or more successive generations.

100 Claims, 9 Drawing Sheets

U.S. PATENT DOCUMENTS

| | | | |
|---|---|---|---|
| 7,343,021 B2 | 3/2008 | Takagi et al. | |
| 2002/0176584 A1 | 11/2002 | Kates | |
| 2003/0133578 A1* | 7/2003 | Durant | 381/60 |
| 2005/0129262 A1 | 6/2005 | Dillon et al. | |
| 2008/0165978 A1 | 7/2008 | Cronin et al. | |
| 2010/0152813 A1 | 6/2010 | Lineaweaver et al. | |
| 2010/0280307 A1 | 11/2010 | Lineaweaver et al. | |
| 2011/0060383 A1 | 3/2011 | Lineaweaver et al. | |
| 2011/0060702 A1 | 3/2011 | Lineaweaver | |

FOREIGN PATENT DOCUMENTS

| | | |
|---|---|---|
| JP | 11-513539 | 11/1999 |
| JP | 2003-6171 | 1/2003 |
| WO | WO 2007/090243 | 8/2007 |

OTHER PUBLICATIONS

Takagi, Hideyuki, "Interactive Evolutionary Computation: Fusion of the Capabilities of EC Optimization and Human Evaluation," Proceedings of the IEEE, Sep. 2001, vol. 89, No. 9, pp. 1275-1298.

International Search Report. PCT/US04/07400. mailed Aug. 27, 2004.

Written Opinion for PCT/US04/07400 dated Aug. 27, 2004.

Canadian Intellectual Property Office, "Office Action," issued in connection with Canadian Patent Application Serial No. 2,518,997, on Apr. 16, 2010 (2 pages).

Skinner, et al., "Speech Recognition with the Nucleus 24 SPEAK, ACE, and CIS Speech Coding Strategies in newly Implanted Adults," Ear & Hearing, vol. 23, No. 3, 208-223, (Jun. 2002).

Skinner, et al., "Nucleus 24 Advanced Encoder Conversion Study: Performance versus Preference," Ear & Hearing, vol. 23, No. 18, 3S-7S, (Feb. 2002).

Wakefield, et al., "Recipient-Directed Design of Speech processor MAPs," in R.T. Miyamoto, ed., Cochlear Implants, Elsevier, International Congress Series, 1273 178-182 (2004).

Wakefield, et al., "Genetic Algorithms for Adaptive Psychopysical Procedures: Recipient-Directed Design of Speech-Processor MAPs," Ear & Hearing, 52S-72S, (Aug. 2005).

Hideyuki Takagi, IEC-based Hearing Aid Fitting, IEEE SM C' 99 Conference Proceedings, Oct. 1999, vol.: 3, 657-662 (6 pages).

International Search Report for International Application No. PCT/IB2010/054105 mailed Jun. 14, 2011 (5 pages).

European Official Communication for European Application No. 04 719 779.3 mailed Apr. 20, 2011 (3 pages).

Japanese Office Action for Japanese Application No. 2006-507068 mailed on Jun. 1, 2010 along with English translation (4 pages).

Japanese Office Action for Japanese Application No. 2006-507068 mailed on Mar. 8, 2011 along with English translation (3 pages).

Japanese Office Action for Japanese Application No. 2006-507068 mailed on Oct. 18, 2011 along with English translation (5 pages).

United States Patent and Trademark Office, "Non-Final Office Action," issued in connection with U.S. Appl. No. 12/358,122, on May 24, 2010 (7 pages).

* cited by examiner

| BIT STRING | MAP PARAMETERS | | | | |
|---|---|---|---|---|---|
| | RATE | # OF MAXIMA | # OF ELECTRODES | COMPRESSION (Q) | AUDIO FILTERING |
| 00000000 | 250 | 4 | 22 | 20 | FLAT |
| 00000001 | 250 | 6 | 22 | 20 | FLAT |
| 00000010 | 250 | 8 | 22 | 20 | FLAT |
| 00000011 | 720 | 6 | 22 | 20 | FLAT |
| 00000100 | 1200 | 8 | 22 | 20 | FLAT |
| 00000101 | 720 | 12 | 22 | 20 | FLAT |
| 00000110 | 250 | 16 | 22 | 20 | FLAT |
| 00000111 | 250 | | | | |
| | 119 OTHER LEGAL COMBINATIONS OF RATE, # OF MAXIMA, # OF ELECTRODES, COMPRESSION Q, AND AUDIO FILTERING | | | | |
| 01111111 | 250 | 4 | 10 | 30 | HIGH CUT |
| 10000000 | 250 | 4 | 22 | 20 | LOW CUT |
| | 126 OTHER LEGAL COMBINATIONS OF RATE, # OF MAXIMA, # OF ELECTRODES, COMPRESSION Q, AND AUDIO FILTERING | | | | |
| 11111111 | 250 | 4 | 10 | 30 | HIGH CUT + LOW CUT |

*FIG. 4*

| NUMBER OF CHNL | STIM. RATE | NO. OF MAXIMA | Q | FAT SHIFT | T-LEVEL BUMP | FILTERS |
|---|---|---|---|---|---|---|
| 8 | 250 | 6 | 10 | DEFAULT SHIFT | DEFAULT BUMP | LOW B |
| 12 | 720 | 8 | 20 | | | LOW CUT |
| 20 | 900 | 12 | | | | HIGH CUT |
| | 1200 | 16 | | | | LOW C |
| | 1800 | 20 | | | | HIGH C |
| | 2400 | | | | | FLAT |

*FIG. 7*

| BINARY | NUMBER OF CHNL. | STIM. RATE | NO. OF MAXIMA | Q | FAT SHIFT | T LEVEL | FILTERS |
|---|---|---|---|---|---|---|---|
| 0000000000 | 20 | 250 | 8 | 10 | 1 | 1 | 1 |
| 0000000001 | 20 | 250 | 8 | 10 | 1 | 1 | 2 |
| 0000000010 | 20 | 250 | 8 | 10 | 1 | 1 | 3 |

*FIG. 8*

| FREQ. INDEX | TABLE 6 | TABLE 7 | TABLE 8 | TABLE 14 | TABLE 15 | TABLE 16 |
|---|---|---|---|---|---|---|
| 0 | 188 | 188 | 188 | 188 | 188 | 188 |
| 1 | 313 | 313 | 313 | 313 | 313 | 313 |
| 2 | 438 | 438 | 438 | 563 | 563 | 563 |
| . | . | . | . | . | . | . |
| 10 | 1563 | 1688 | 1688 | 3438 | 4063 | 4813 |
| 11 | 1813 | 1938 | 1938 | 4188 | 5063 | 6188 |
| 12 | 2063 | 2188 | 2313 | 5188 | 6313 | 7938 |
| 13 | 2313 | 2563 | 2688 | 6313 | 7938 | |
| . | . | . | . | . | | |
| 20 | 6063 | 6938 | 7938 | | | |
| 21 | 6938 | 7938 | | | | |
| 22 | 7938 | | | | | |

*FIG. 9*

USING A GENETIC ALGORITHM TO FIT A COCHLEAR IMPLANT SYSTEM TO A PATIENT

CROSS-REFERENCE TO RELATED APPLICATIONS

This application is a continuation-in-part of and claims priority to U.S. patent application Ser. No. 10/385,880, entitled "Cochlear Implant Map Optimization With Use Of A Genetic Algorithm," filed Mar. 11, 2003 now U.S. Pat. No. 6,879,860, and is a continuation-in-part of and claims priority to PCT Application No. PCT/US2004/007400, entitled, "Cochlear Implant System With Map Optimization Using A Genetic Algorithm," filed on Mar. 11, 2004, now pending, the entire contents and disclosures of which are hereby incorporated by reference.

This application is related to U.S. Pat. Nos. 4,532,930, 5,277,694, 6,123,660, 6,162,169, 6,537,200, 6,565,503, 6,575,894, and 6,697,674. The entire disclosure and contents of the above patents are hereby incorporated by reference herein.

BACKGROUND

1. Field of the Invention

The present invention relates generally to cochlear implant systems and, more particularly, to using a genetic algorithm to fit a cochlear implant system to a patient.

2. Related Art

Many medical devices have structural and/or functional features which are to be adjusted for an individual patient. The process by which a medical device is tailored or customized for the specific needs of a patient is commonly referred to as fitting. One type of medical device which is typically fitted to individual recipients is a cochlear™ implant system.

Cochlear™ implant systems provide the benefit of hearing to individuals suffering from severe to profound hearing loss. Hearing loss in such individuals is often due to the absence or destruction of the hair cells in the cochlea which transduce acoustic signals into nerve impulses. Cochlear™ implant systems essentially simulate the auditory nerves by directly delivering electrical stimulation to the auditory nerve fibers. This causes the brain to perceive a hearing sensation resembling the natural hearing sensation normally delivered by the auditory nerve. Examples of cochlear implant systems are described, by way of example, in U.S. Pat. Nos. 4,532,930, 6,537,200, 6,565,503, 6,575,894, and 6,697,674, among others.

Conventional cochlear™ implant systems commonly include an external assembly directly or indirectly attached to the body of the patient (sometimes referred to herein as the recipient), and an internal assembly which is implanted in the patient. The external assembly typically comprises one or more microphones for detecting sound, a speech processing unit that converts detected sound into an electrical coded signal, a power source, and an external transcutaneous transfer coil. The internal assembly typically comprises an internal transcutaneous transfer coil, a stimulator unit located within a recess of the temporal bone of the recipient, and an electrode array positioned in the recipient's cochlea. Completely implantable cochlear implant systems having functionally similar components are under development.

In addition to providing electrical stimulation, some cochlear™ implant systems also include a mechanical stimulation mode of operation. Such so called mixed-mode systems offer rehabilitation by mechanically stimulating a portion of a patient's auditory pathway, either acoustically or physically. For example, there have been approaches to offer rehabilitation with conventional hearing aids via the application of an amplified acoustic signal to the external auditory canal, or by physically stimulating an ossicle of the middle ear or the inner ear via mechanical or hydromechanical stimulation.

Modern cochlear implant systems provide a wide variety of fitting options that can be customized for an individual patient. Because patients are heterogeneous, each patient requires a different set of parameters to maximize speech reception and patient satisfaction. The task of the clinical professional, usually an audiologist, is to select a set of parameters, commonly referred to as a parameter map or, more simply, a MAP, that will provide the best possible speech reception for an individual patient. Because there may be hundreds or thousands of possible parameter maps, it is impractical to experience all of the alternatives and to evaluate the performance of each alternative for an individual patient. Nor is it possible to identify an optimal parameter map by prescription based on a limited set of measurements as is, for example, the case in fitting eyeglasses. Because parameters of cochlear implant systems often interact non-linearly and non-monotonically, it is also not possible to sequentially optimize parameters one at a time, adjusting each in succession to its optimal value.

As a result, clinicians have adopted a variety of approaches for fitting the cochlear implant systems to a patient. Some simply set the parameters to default valves regardless of the individual patients. Others adopt preferred parameter maps, which they believe are good, if not best, for many or most patients. These may be based on personal experience, published performance data, or intuition. Some clinicians evaluate a limited set of alternatives adjusting individual parameters based upon measured perceptual limitations and inferred relationships among the parameters. These approaches are time consuming, costly, and unreliable, and typically fail to achieve the optimal outcome for individual patients.

SUMMARY

In one aspect of the invention, a method for at least partially fitting a cochlear implant system to a patient is described, comprising: executing a genetic algorithm to select values for a subset of one or more parameters selected from a plurality of parameters for which values are to be selected to fit the implant, wherein said genetic algorithm is operable to generate one or more successive generations of values for said parameter subset; and determining, based on patient feedback, said values of said values for said parameter subset in each of said one or more successive generations.

In another aspect of the invention, an apparatus for at least partially fitting a cochlear implant system to a patient is described, comprising: means for executing a genetic algorithm to select values for a subset of one or more parameters selected from a plurality of parameters for which values are to be selected to fit the implant, wherein said genetic algorithm is operable to generate one or more successive generations of values for said parameter subset; and means for determining, based on patient feedback, said values of said values for said parameter subset in each of said one or more successive generations.

BRIEF DESCRIPTION OF THE DRAWINGS

FIG. 4 is a logical block diagram illustrating a manner in which a parameter map formed of a bit string represents parameter values, in accordance with one embodiment of the present invention.

FIG. 7 is a table of seven parameters that can be determined using the subject algorithm, and the possible values of each parameter, in accordance with one embodiment of the present invention.

FIG. 8 is a table of a partial listing of 10-bit maps used to determine the parameters of FIG. 7, in accordance with one embodiment of the present invention.

FIG. 9 is a table of a partial listing of frequency allocations to various channels to illustrate FAT shifting, in accordance with one embodiment of the present invention.

DETAILED DESCRIPTION

Figure 1:
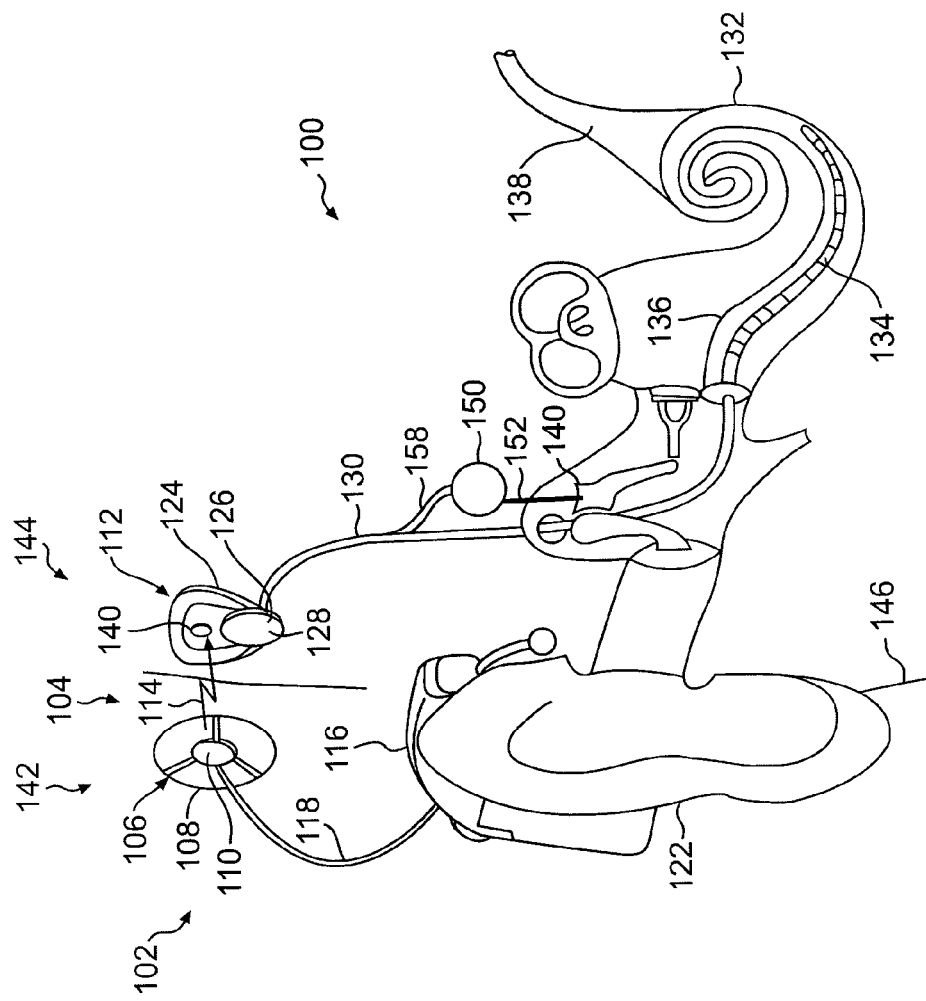
FIG. 1 is a simplified perspective view of internal and external components of an exemplary cochlear implant system shown in their operational position on a patient, in accordance with one embodiment of the present invention.

It is advantageous to define several terms before describing the invention. It should be appreciated that the following definitions are used throughout this application. Where the definition of terms departs from the commonly used meaning of the term, applicant intends to utilize the definitions provided below, unless specifically indicated.

For the purposes of the present invention, the term "a number of spectral maxima periodically chosen for representation" refers to an integer value which determines, at any moment, how many peaks in the audio spectrum should be represented by corresponding electrical pulses delivered to channels of a cochlear implant.

For the purposes of the present invention, the term "a mapping of sound pressure to stimulus current for each said respective channels" refers to the mathematical algorithm which determines an appropriate intensity for electrical stimulation as derived from the intensity of an audio signal.

For the purposes of the present invention, the term "front end filtering of audio from a microphone" refers to any process which alters the frequency spectrum of an audio signal derived from a microphone.

For the purposes of the present invention, the term "automatic gain control threshold" refers to the softest sound intensity which activates an automatic gain control, causing it to alter the amplification of an audio signal.

For the purposes of the present invention, the term "compression ratio" refers to the relationship between change in intensity at the input of a signal processing stage to the corresponding change in intensity at its output, usually expressed a ratio of logarithmic units, e.g. decibles per decibel.

For the purposes of the present invention, the term "attack and release times" refers to the speed with which a gain adjustment stage, such as an automatic gain control or compressor, reduces or increases the gain respectively.

For the purposes of the present invention, the term "threshold levels" in the context of mapping of sound pressure to stimulus current for each channel refers to the lowest electrical stimulus intensity which results in an audible sensation.

For the purposes of the present invention, the term "compression curves" in the context of mapping of sound pressure to stimulus current for each channel refers to the mathematical relationship between an input sound intensity and the intensity of a corresponding electrical stimulus used to represent the sound.

For the purposes of the present invention, the term "loudness parameter" refers to any parameter of a signal processing path which alters the perceived loudness of a stimulus, either electrical or mechanical.

For the purposes of the present invention, the term "long term loudness balance parameters" refers to the relative loudness of two percepts, one elicited electrically and one elicited mechanically, averaged over a time period which is long compared to phonemic intervals.

For the purposes of the present invention, the term "short term gain manipulations" refers to any change in processing gain which occurs over a time interval which is short compared to the duration of a typical sentence.

For the purposes of the present invention, the term "signal-dependent gain adjustments" refers to any adjustment of gain which depends upon any aspects of the input or output signal of a signal processing stage.

For the purposes of the present invention, the term "adjustments to minimize cross-modal masking" refers to any adjustment of a processing parameter which acts to reduce the extent to which presence of a stimulus of one modality (e.g. electrical) alters the loudness or discriminability of a percept elicited by a stimulus of another modality (e.g. mechanical).

For the purposes of the present invention, the term "adjustments to emphasize speech features" refers to any adjustment of one or more processing parameters which acts to make particular aspects of a speech utterance more salient to a listener.

For the purposes of the present invention, the term "frequency domain parameters" refers to any parameter which is derived from aspects of the frequency spectrum of an audio signal.

For the purposes of the present invention, the term "frequency boundaries allocated to electrical and mechanical stimulation" refers to the frequencies which define the spectral extent of an input audio signal which is processed ultimately to generate a corresponding electrical or mechanical stimulus.

For the purposes of the present invention, the term "allocation of frequency subbands in each domain" refers to the process of determining which frequency ranges, within an encompassing range of frequencies, are selected for control of corresponding processing parameters such as current intensity for a corresponding electrical channel.

For the purposes of the present invention, the term "time domain parameters" refers to any parameter which is derived from aspects of the time domain representation of an audio signal which means the function describing intensity versus time.

For the purposes of the present invention, the term "adjusting electrical periodicity of pulse timing to be synchronized with mechanical signal fluctuations" refers to any process whereby the onset times or durations of electrical pulse stimuli are modified in accordance with aspects of an audio signal so as to achieve a preferred temporal relationship between the electrical stimulus events and mechanical stimulus events.

For the purposes of the present invention, the term "binaural parameters" refers to any parameter which influences stimuli to each of two ears whether of the same or different modalities.

For the purposes of the present invention, the term "adjustment of stimulus timing to suppress echo" refers to any manipulation which acts to reduce the perception of an echo by a listener.

For the purposes of the present invention, the term "adjustment of stimulus timing to improve localization" refers to any manipulation of a signal or stimulus which acts to improve a listener's ability to determine the spatial location of a sound's origin.

For the purposes of the present invention, the term "adjustment of stimulus timing to improve sound source segregation" refers to any manipulation of a signal or stimulus which acts to improve a listener's ability to hear independently a signal from a particular sound source which is occurs concurrently with one or more signal(s) from competitive sound sources.

For the purposes of the present invention, the term "selecting values for parameters not included in said subset of at least one parameter by a method that does not use a genetic algorithm" refers to any process whereby values are chosen for parameters that are not adjusted or selected by means of a genetic algorithm, including clinical traditional fitting procedures.

Embodiments of the present invention are described below in connection with one embodiment of a medical implant such as a cochlear™ prosthesis (also referred to as a cochlear™ implant system, cochlear™ prosthetic device and the like; generally referred to herein as a "cochlear implant system"). As used herein, the term "cochlear implant system" refers to partially- or completely-implantable devices that provide electrical stimulation as well as devices that provide both, electrical and mechanical stimulation to a patient to improve and/or provide hearing sensations.

Electrical stimulation may be provided, for example, to a patient's cochlea, or other parts of a patient's auditory pathway. Mechanical stimulation may be provided acoustically, that is, via airborne pathways, or physically such as with a mechanical transducer, or other electromechanical device now or later developed, to any point in the auditory pathway. Accordingly, cochlear implant systems which may be at least partially fitted using a genetic algorithm of the present invention may provide single-mode (electrical) stimulation or mixed-mode (electrical and mechanical) stimulation. Mixed-mode stimulation encompasses, for example, providing electrical and mechanical stimulation to the same ear (sometimes referred to as "hybrid stimulation"); electrical stimulation to one ear and mechanical stimulation to the other ear (sometimes referred to as "bimodal stimulation"); and hybrid stimulation to one ear and either mechanical and/or electrical stimulation in the other ear (sometimes referred to as "combined stimulation").

FIG. 1 is a schematic diagram of an exemplary cochlear implant system 100 which may be fitted to an individual patient in accordance with embodiments of the present invention. This embodiment of cochlear implant system 100 has single- and mixed-mode operational capabilities. With regard to an electrical stimulation mode of operation, cochlear implant system 100 provides direct electrical stimulation of auditory nerve cells to bypass absent or defective hair cells that normally transduce acoustic vibrations into neural activity. In this illustrative embodiment, cochlear implant system 100 comprises external component assembly 142 which is directly or indirectly attached to the body of the patient, and an internal component assembly 144 which is temporarily or permanently implanted in a patient. External assembly 142 typically comprises at least one audio pickup device such as a microphone (not shown) for detecting sounds, a speech processing unit 116 that converts the detected sounds into a coded signal, a power source (not shown), and an external transmitter unit 106. External transmitter unit 106 comprises an external coil 108, and, preferably, a magnet 110 secured directly or indirectly to external coil 108. Speech processor 116 processes the output of the audio pickup devices that may be positioned, for example, by the ear 122 of the recipient. Speech processor 116 generates stimulation signals which are provided to external transmitter unit 106 via cable 118.

Internal components 144 comprise an internal receiver unit 112, a stimulator unit 126, and an electrode array 134. Internal receiver unit 112 comprises an internal receiver coil 124 and a magnet 140 fixed relative to internal coil 124. Internal receiver unit 112 and stimulator unit 126 are hermetically sealed within a housing 128. Internal coil 124 receives power and data from transmitter coil 108. A cable 130 extends from stimulator unit 126 to cochlea 132 and terminates in an electrode array 134. The received signals are applied by array 134 to basilar membrane 136 thereby stimulating auditory nerve 138. Typically, the electrodes differentially activate auditory neurons that normally encode differential pitches of sound.

Collectively, transmitter antenna coil 108 (or more generally, external coil 108) and receiver antenna coil 124 (or, more generally internal coil 124) form an inductively-coupled coil system of a transcutaneous transfer apparatus 102. Transmitter antenna coil 108 transmits electrical signals to the implantable receiver coil 124 via a radio frequency (RF) link 114. Internal coil 124 is typically a wire antenna coil comprised of at least one and preferably multiple turns of electrically insulated single-strand-or multi-strand platinum or gold wire. The electrical insulation of internal coil 124 is provided by a flexible silicone molding (not shown). In use, implantable receiver unit 112 may be positioned, for example, in a recess of the temporal bone adjacent ear 122 of the recipient.

Regarding the mechanical mode of operation, cochlear implant system 100 provides, in this illustrative embodiment, direct mechanical stimulation to the patient's inner ear.

Electromechanical transducer 150 is coupled to the middle ear or inner ear using any technique now or later developed. Transducer 150 stimulates the impaired inner ear by direct mechanical coupling via coupling element 152 to a middle ear ossicle or via an air gap coupling for implantable transducers which are electromagnetic, for example. In this illustrative embodiment, electromechanical transducer 150 is coupled to incus 140. One example of transducer 150 is described in U.S. Pat. No. 5,277,694 which is hereby incorporated by reference herein. In the embodiment of a hermetically tight transducer described therein, a housing wall of the transducer is designed as a vibrating membrane which, together with a piezoelectric ceramic wafer applied to the inside thereof, comprises an electromechanically active composite element, the mechanical vibrations of which are transmitted to the ossicular chain via a coupling rod 152 permanently attached to the outside of the membrane. Optionally, coupling rod 152 can be attached to the membrane via a coupling element which is connected to the coupling rod. Alternatively, transducer 150 can be implemented as described in U.S. Pat. No. 6,123,660 which is hereby incorporated by reference. In such an embodiment, a permanent magnet is attached to the inside of the piezoelectric ceramic wafer to interact with an electromagnetic coil, such as an electromagnetic transducer. Such a combined piezoelectric-electromagnetic transducer is advantageous in particular with respect to a wide frequency band and achieving relatively high vibration amplitudes with comparatively small supplied energy.

In an alternative embodiment, transducer 150 can be an electromagnetic transducer arrangement as is described in commonly owned U.S. Pat. No. 6,162,169 which is hereby incorporated by reference herein. In such an embodiment, the transducer arrangement comprises a housing which can be fixed at the implantation site with reference to the skull, with a mechanically stiff coupling element which can move relative to the housing. In the housing there is an electromechanical transducer which to vibrates the coupling element.

The above signal processing components are controlled by a microcontroller included, for example, in speech processor 116. The microcontroller includes a storage area in which patient-specific audiologic adaptation parameters and the audiometry parameters of the above-noted signal generator are stored. The microcontroller and associated data storage may be implantable, such as within stimulator unit 126. In such embodiments, the programmable data are sent to the microcontroller via telemetry unit 102.

As noted, there may be a substantial quantity of parameters which may be customized to optimally fit a cochlear implant system to an individual patient. As will be described below, not all parameters may be selected to obtain values with the generic algorithm. The selected subset of parameters and their respective values is collectively and generally referred to herein as a "parameter map," a "cochlear map" or "MAP." Because of the quantity of parameters which may be selected, and because such parameters may interact non-linearly and non-monotonically, selection of the parameter map which will provide the best possible outcome for an individual patient has been heretofore exceedingly difficult or impossible to obtain.

Examples of parameters include, for example, the speech strategy implemented in the cochlear implant system. Within any given speech strategy a great many parameters and parameter values may be specified to tailor the encoding and stimulation for an individual patient. Examples of parameters and parameter values that may be selected for a speech strategy include but are not limited to the number of frequency bands (channels) represented, the intracochlear and/or extracochlear electrodes which are to be associated with each channel, the pulse repetition rate for each channel, the pulse width for each channel, the number of spectral maxima periodically chosen for representation, the mapping of sound pressure to stimulus current for each channel (thresholds, comfort levels and compression curves), front end filtering of the audio from the microphone (pre-emphasis), and automatic gain control threshold, compression ratio, and attack and release times.

In cochlear implant systems such as system 100 described above which provide electrical and mechanical stimulation, additional parameters may be selected to tailor the cochlear implant system to an individual patient. Such parameters include, but are not limited to, loudness parameters such as long term loudness balance (that is, electrical and mechanical gains), short term gain manipulations, particularly signal-dependent gain adjustments. Such gain adjustments include, for example, adjustments to minimize cross-modal masking, and adjustments to emphasize speech features such as frication or voicing.

Additional parameters may include frequency domain parameters. Such parameters include, for example, overall frequency boundaries allocated to electrical and mechanical stimulation, slopes of filtering at the boundaries of each stimulation signal, allocation of frequency subbands (both quantity and boundaries) in each domain, etc. Also, filtering of the mechanical signal within the passband, for example, to match the hearing loss or for other purposes.

Additional parameters may also include time domain parameters. Such parameters include, for example, adjusting electrical periodicity of pulse timing to be synchronized with the mechanical signal fluctuations, adjusting delays in the electrical stimulus to compensate for missing propagation delays of various middle ear and inner ear pathways, etc.

Additional parameters may also include binaural parameters. Such parameters include, for example, adjusting stimulus timing to present interaural timing cures, adjustment of stimulus timing to suppress echo, improve localization, or improve sound source segregation, etc.

As used herein, the term 'parameter values' generally and collectively refers to values of parameters, whether selectable options are programmed on or off, and in general to any choices that are made during a fitting procedure. As one or ordinary skill in the art would appreciate, the above parameters are an example of mixed-mode parameters which may be selected and tailored to optimally fit a single-mode (electrical stimulation) and for mixed-mode (electrical and mechanical stimulation) cochlear implant system to a patient.

As noted, embodiments of the present invention are directed to utilizing a genetic algorithm to fit a cochlear implant to a patient. A genetic algorithm is an adaptive procedure, based on a model of biological evolution, which can be used to find optimal solutions to a problem. The procedure implements aspects of evolution, including "natural selection," "procreation with inheritance," and "random mutation." The underlying premise is that the evolutionary process will, over multiple generations, produce an optimal "organism;" that is, an organism that it is most likely to survive and procreate.

Each iteration of a genetic algorithm procedure begins with one generation of organisms and produces a succeeding generation. This typically involves two steps, selection and procreation. Selection involves the choosing of a subset of organisms as potential "parents" of the organisms of the succeeding generation ("children"). Procreation involves the creation of children from the selected sets of potential parents (usually pairs).

In genetic algorithms, selection operates on strings of binary digits stored in the computer's memory, and over time, the functionality of these strings evolves in much the same way that natural populations evolve. Genetic algorithms are capable of evolving surprisingly complex and interesting structures. For example, such structures may represent not only solutions to problems, but also strategies for playing games, visual images, or even simple computer programs. The Darwinian theory of evolution depicts biological systems as the product of the ongoing process of natural selection. Likewise, genetic algorithms allow the utilization of computers to evolve solutions over time, instead of designing them by hand. Because almost any method, theory or technique can be programmed on a computer, this implies an approach to problem solving that can be, at least partially, automated by a computer.

The basic idea of a genetic algorithm is that first a population of organisms is created in a computer (typically with genes stored as binary strings in the computer's memory), and then the population is evolved with use of the principles of variation, selection, and inheritance. There are many ways of implementing a genetic algorithm, but the most basic is that suggested by J. H. Holland, in Adaptation in Natural and Artificial Systems, Univ. of Michigan Press, Ann Arbor, Mich., 1975, reprinted by MIT Press, Cambridge, Mass., 1992, which is hereby incorporated by reference herein.

Each of a group of organisms in a "generation" is assigned a fitness value by a fitness function. On the basis of these fitness values, the selection function ranks the organisms. After selection, genetic operators are applied probabilistically; some organisms may have bits in their genes mutated from a 1 to a 0 or a 0 to a 1, and parts of different organisms' genes are then combined into new ones. The resulting population comprises the next generation and the process repeats itself.

The fitness function is the primary place in which a traditional genetic algorithm is tailored to a specific problem. Once all organisms in the population of a particular generation have been evaluated, their fitnesses are used as the basis for selection. Selection is implemented by eliminating low-fitness individuals from the population, and inheritance is often implemented by making multiple copies of high-fitness individuals. Genetic operators such as mutation (flipping individual bits) and crossover or inheritance (exchanging sub-strings of two organisms to obtain two offspring) are applied probabilistically to the selected individuals to produce new organisms. By replacing members of the old generation with such new organisms, new generations are produced so that the old generation is completely replaced ("synchronously"), or so that the new and old members of the generation overlap ("asynchronously"). The genetic operators have been shown to generate new organisms that, on average, are better than the average fitness of their parent organisms. Therefore, when this cycle of evaluation, selection, and genetic operations is iterated for many generations, the overall fitness of the population generally improves, on average, and the organisms in the population represent improved "solutions" to whatever problem was posed in the fitness function.

Selection can be performed in any of several ways. It can arbitrarily eliminate the least fit organisms of the population and make one copy of all the remaining organisms, it can replicate organisms in direct proportion to their fitness, or it can scale the fitnesses in any of several ways and replicate organisms in direct proportion to their scaled values (a more typical method). Likewise, the crossover operator can pass on both offspring to the new generation, or it can arbitrarily choose one to be passed on. These and other variations of the basic algorithm are well known in the art.

As noted, embodiments of the present invention is directed to using a genetic algorithm to optimally fit a cochlear implant to a patient. Specifically, embodiments of the present invention are directed to executing a genetic algorithm to select values for a subset of all the parameters for which values are to be selected to at least partially fit the cochlear implant system. In one embodiment, the genetic algorithm operates to generate successive generations of multiple groups of values for this parameter subset. Patient feedback during execution of such a genetic algorithm determines the multiple groups of subset values in each of the successive generations. Selection is thus based on the subjective listening judgment of the patient during execution of the genetic algorithm. In each generation, less than all (for example, half) of the groups of values for the parameter subset are selected and used to determine a larger number of groups of values for the next generation (e.g., twice as large, if it is desired that all generations be of the same size). Values for the parameters outside the subset are selected by any method now or later developed that does not use a genetic algorithm. Typically, most of the parameters are not selected by using a genetic algorithm. For example, in one illustrative embodiment, the subset of parameters selected by a genetic algorithm for the electrical stimulation mode of operation include parameters relating to those characteristics commonly considered by clinicians to be important in the fitting process: rate, number of channels and filtering characteristics.

In a genetic algorithm, an 'organism' is defined by a set of $N_b$ 'genes' (bits), with the number of possible unique organisms is $2^{Nb}$. In connection with the invention, the organism to be optimized is a parameter or cochlear MAP. As noted, such a MAP is a collection of values for a set of parameters. In the exemplary cochlear map 300 illustrated in FIG. 3A, there is a set of 8 binary genes 304A–304H ($N_b=8$) so MAP 300 is defined by a gene set or string of 8 bits 304 forming 256 possible MAPs 300. MAP 300 is an example of the organisms 202 shown in FIGS. 2A–2E are described below. Each of the 8 bits 304 may be used to individually or collectively designate several parameters for cochlear implant system 100. In the example shown in FIG. 3A, three such parameters 306A–306C are designated. Three bits 304A–304C are used to select a parameter 306A of stimulus rate (the rate, in Hz, at which high-energy channels are selected and stimulus pulses are delivered to groups of N electrodes), three bits 304D–304F are used to select a parameter 306B of spectral maxima counts (the number N of electrodes periodically selected to be stimulated, representing the N frequency bands with the highest energy at the time), and the remaining two bits 304G–304H select a parameter 306C of the quantity of channels or frequency bands, used to represent the sound spectrum. Other parameters are assumed to be constant or derived from one of the three represented parameters 306; they are fitted using traditional methods. As discussed in more detail below, the number of bits for each cochlear map 300 and the number of parameters 306 defined by the MAPs may be different in alternative embodiments.

Figure 3A:
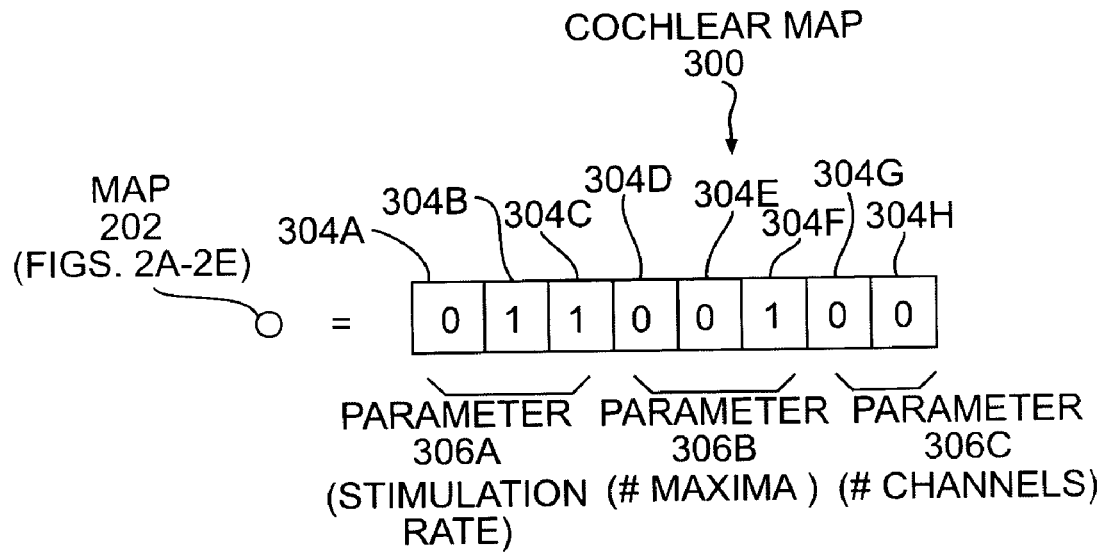
FIG. 3A depicts how specific bits in a bit string can represent values of respective parameters, in accordance with one embodiment of the present invention.

In a genetic algorithm a 'generation' can be considered to be a set of one or more organisms. Generally, the number of organisms $N_g$ is constant from generation to generation although that need not be the case. In one embodiment, the initial generation comprises a selection of 8 different MAPs as illustrated in FIG. 3A, which span the parametric ranges. These MAPs may be completely random. Alternatively, some or all MAPs of the initial generation may be the preferences of the patient or clinicians, or may be selected from the results of a previous execution of the method, as discussed in greater detail below.

A 'fitness function' is used to evaluate each of the organisms in each generation. The fitness function identifies which organisms will survive to become parents and procreate, and which of the organisms die. Generally, the number of survivors is constant from generation to generation, although that need not be the case. In one embodiment, a fitness function is used that causes half of the organisms survive.

Preferably, the fitness function is a subjective listening test performed by the patient. For example, the patient may listen to speech presented through each of the MAPs in a generation, and selects, for example, half of the MAPs that produce the best intelligibility. Note that the patient need not rank groups of subset values from best to worst. With eight groups per generation, for example, the patient simply has to choose the four he or she likes best.

Alternatively, the fitness of a MAP may be determined entirely, or in part, from objective measures, that is, measurements not involving a judgment by the patient, such as cortical or brainstem evoked potentials measured from the patient, the patient's ability to repeat a speech token, the quality of a the patient's speech while listening to his/her own speech with a selected cochlear map, results of an objective speech reception test, or expert knowledge about known beneficial parameter combinations.

Figures 2A, 2B:
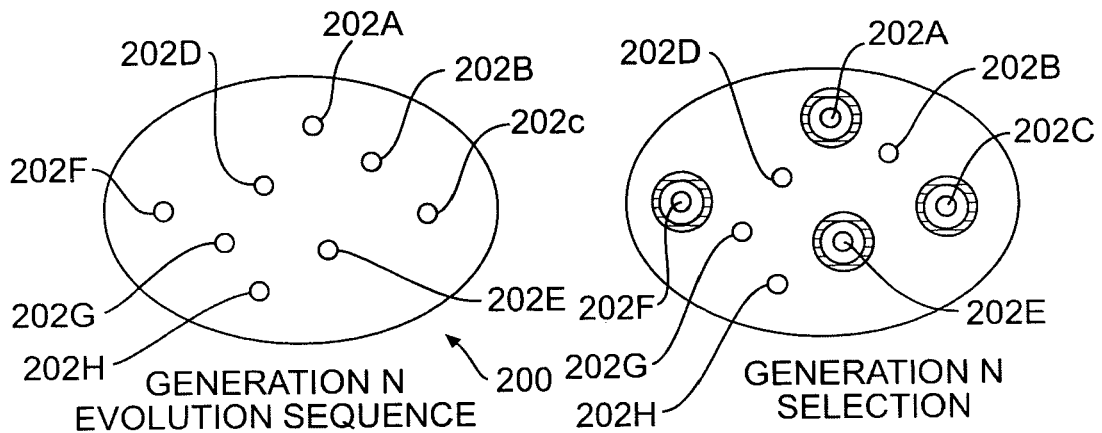
FIGS. 2A–2E depict successive states in the performance of the genetic algorithm for a specific generation in accordance with the principles of one embodiment of the present invention.
Figure 2C:
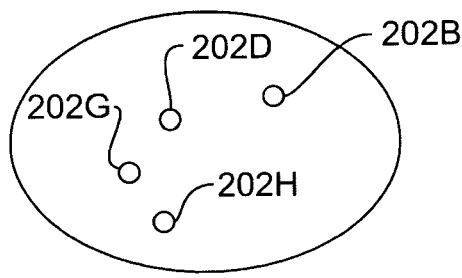
Figures 2D, 2E:
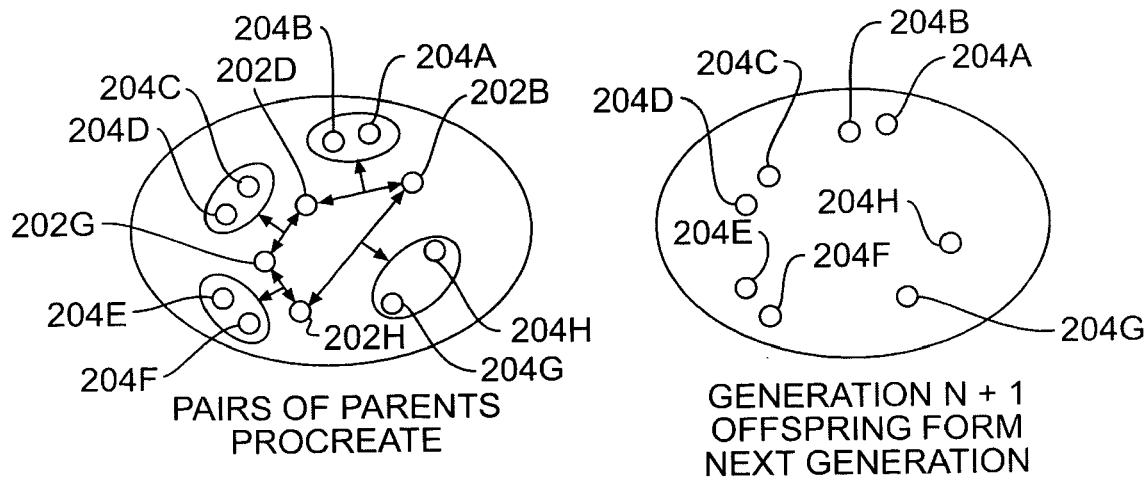

'Reproduction' involves three separate operations: pairing of parents, inheritance, and mutation. For example, FIG. 2A depicts an arbitrary generation N in an overall sequence 200 that has evolved to contain 8 organisms or individuals 202A–202H. The 'fitness function' rejects four of these organisms: 202A, 202C, 202E and 202F (these organisms are circled in generation selection 204 illustrated in FIG. 2B). FIG. 2C showing the survivor organisms 202B, 202D, 202G and 202H in the survival of the fittest illustration 206. The survivors are then paired, as shown in FIG. 2D, with each survivor 202B, 202D, 202G and 202H mating with two other survivors. Each pair produces two children 204A–204H. The 8 children 204 make up generation N+1, as shown in FIG. 2E.

In one illustrative embodiment, a round-robin algorithm is used to identify pairs of parents 202 in each generation, with each pair producing several children 204. In one particular embodiment, each pair of parents 202 produces two children 204. For example, 8 MAPS can be arranged into four pairs of parents 202 resulting in a new generation of 8 children 204. Each child 204 inherits some of its 'genes' from each parent 202. For example, the string of bits of each MAP can be partitioned by boundaries into sub-strings that constitute "genes." Finally, after reproduction, each gene is, optionally, subject to random inversion (mutation). Preferably the probability of each mutation is small. Typically this probability may range from 1 to 10%. In one embodiment, the mutation probability is approximately 3%.

In one embodiment, the genetic algorithm includes performing reproduction on an initial generation several times, and then using the last or final generation to program a cochlear implant system such as system 100. Embodiments of this process are described next below. FIG. 3A is an illustration of an organism 300 represented by the leftmost circle 202 in FIG. 3A and corresponding to the circles in FIGS. 2A–2E. In this example, organism 202 is a MAP 300 defined by a set of 8 binary bits or genes 304A–304H. In this case, the 8 bits 304 have been partitioned into three sub-strings 306A–306C, each corresponding to a parameter. The first set 306A of 3 bits 304A–304C represents 1 of 8 stimulation rates, the second set 306B of 3 bits 304D–304F represents 1 of 8 maxima counts, and third set 306C of 2 bits 304G–304H represents 1 of 4 channel counts. For each of the 8 stimulation rates, a corresponding set of threshold (T) and comfort (C) levels, one for each electrode, is also selected. Ts and Cs may be determined, for example, by clinician measurement at the corresponding rate, or by inference, using a mathematical loudness model, from Ts and Cs measured at a single standard rate. For each MAP 300 appropriate T and C levels are used for each stimulation rate.

Figure 3B:
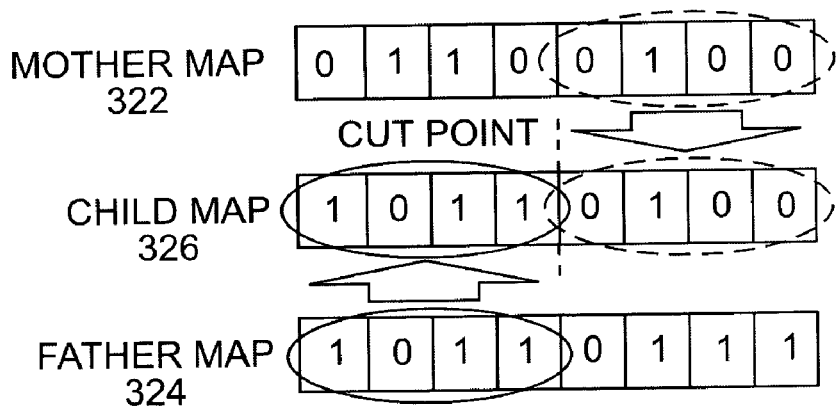
FIG. 3B illustrates how two 'parent' bit strings reproduce, in accordance with one embodiment of the present invention.
Figure 3C:
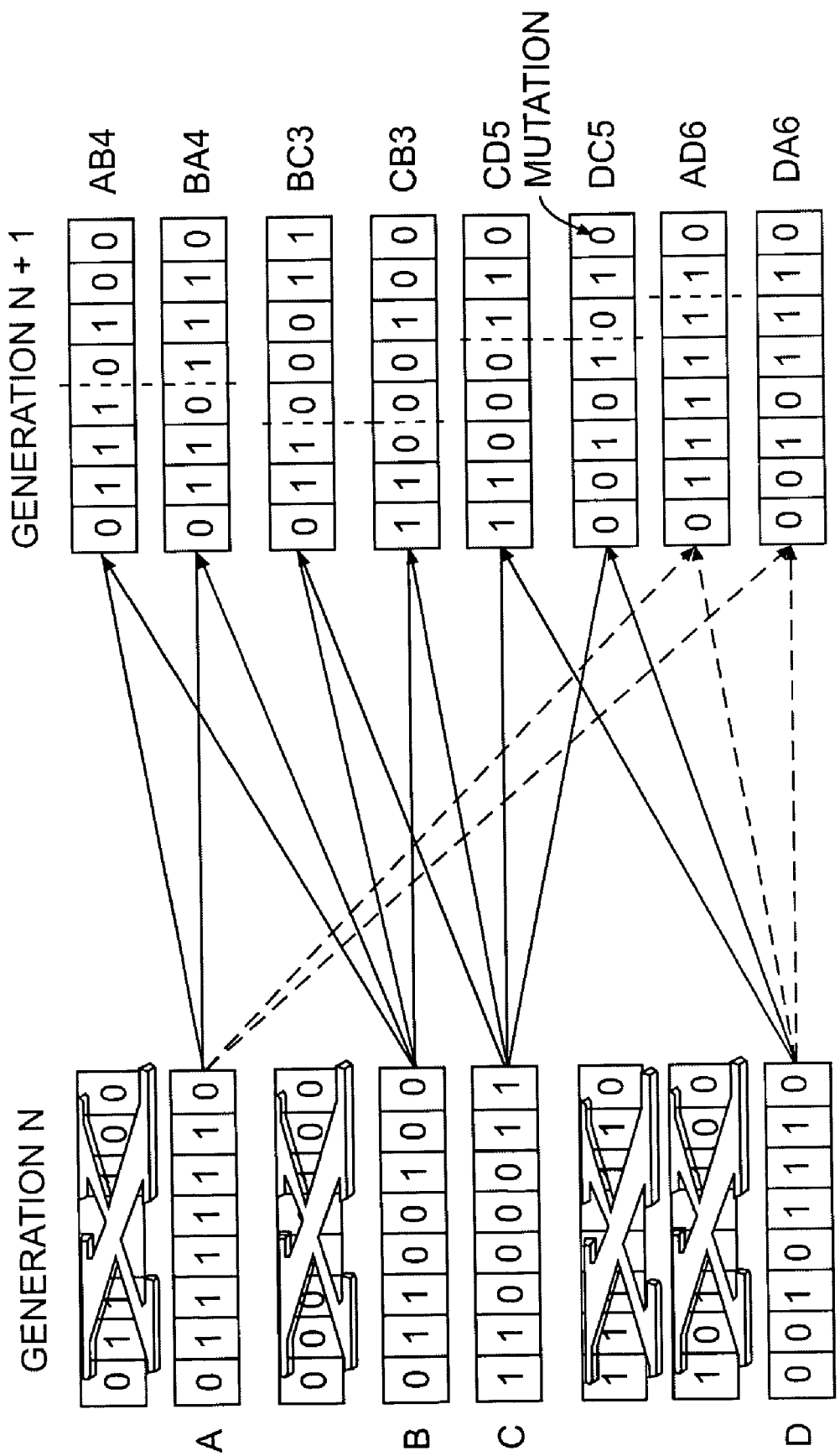
FIG. 3C is a logical block diagram showing how organisms of a generation survive and reproduce to give rise to organisms in a successive generation.
Figure 3D:
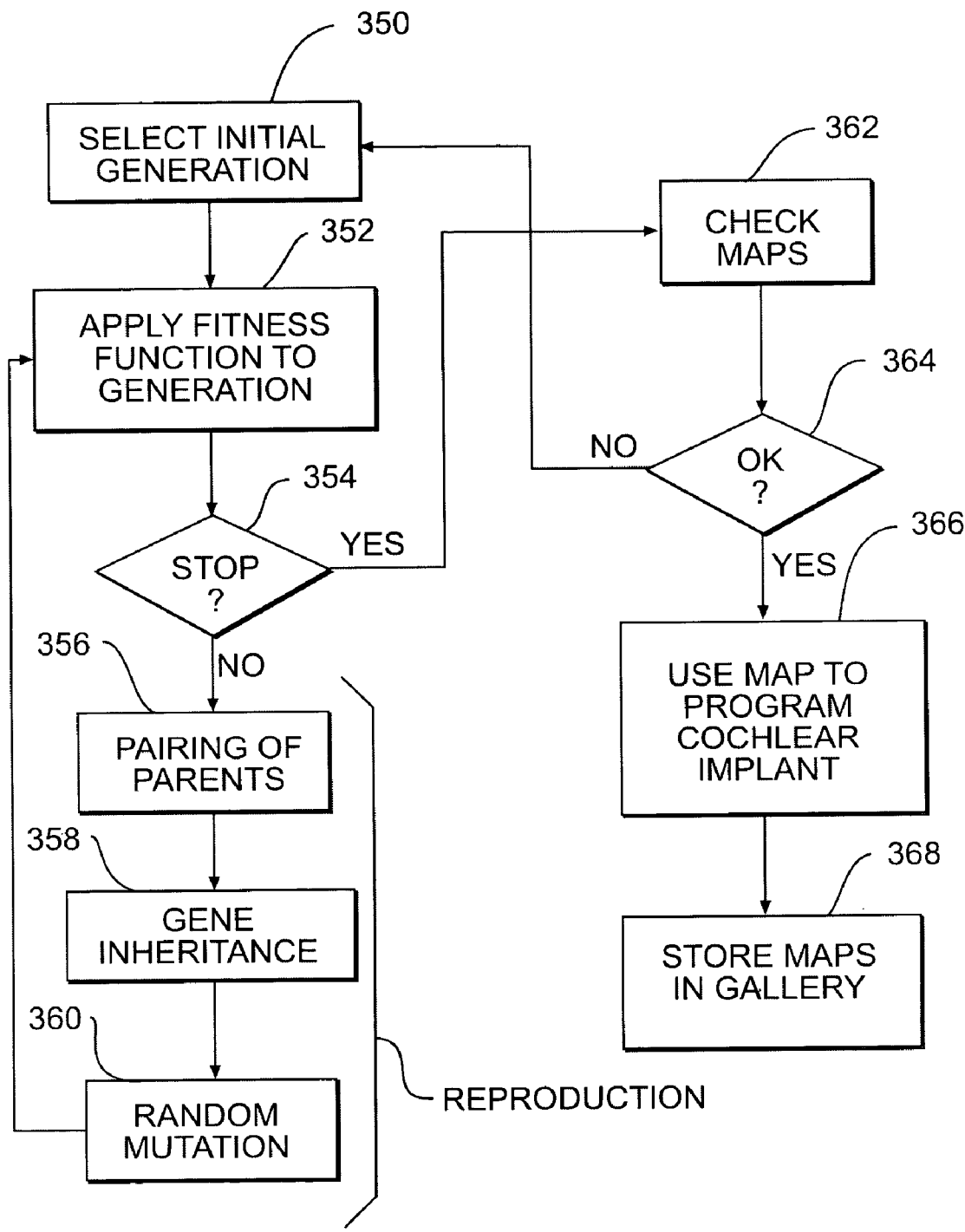
FIG. 3D is a flow chart of the operations performed to determine a parameter map using a genetic algorithm, in accordance with one embodiment of the present invention.

FIG. 3D is a flow chart of the operations performed to determine a MAP using a genetic algorithm, in accordance with one embodiment of the present invention. Referring to FIG. 3D, initially at block 350, a generation of eight MAPs 300 is selected. Initialization requires the selection of first generation of designs. This selection may be performed by selecting at random from among the set of possible MAPs. Preferably, in order to insure that this initial MAP set has a sufficient measure of heterogeneity, its diversity is computed. In one embodiment, diversity is defined as the average Hamming distance between the various MAPS, and it ranges between 0 and 1, with 1 indicating maximum diversity and 0 indicating minimum diversity. If the diversity is below a threshold, for example, 0.53, then the initial generation has an insufficient diversity, and a new set of MAPs is selected. Moreover, pre-selected MAPs may also be included among the MAPs of the first generation. These pre-selected MAPs may be drawn from prior runs of the fitting procedure, MAPs from the implant patient's gallery or MAPs selected by a clinician based on his experience, suggestions and recommendations from others, etc.

Next, at block 352 the fitness function is applied to the initial generation. That is, the parameters corresponding to the eight MAPs 300 are sequentially programmed into a cochlear system or emulator and tests are performed to determine which subset of the generation provides better results. As described above, these tests may be subjective tests based on the perception of the patient, objective tests during which some physiological measurements are taken, or a combination of both types of tests.

For example, as part of the fitness function, the patient may be asked to listen to a speech token for each of the eight MAPs. The patient may listen to each token as many times as the patient prefers. In one embodiment, the tokens are selected from a library of relatively long audio files (e.g., 2 minutes). Each file in such a library may include, for example, a single speaker reading aloud from a newspaper or a passage from an audio book. In one embodiment, the patient listens to the whole file. In another embodiment, the file is partitioned into shorter segments of random lengths. Each segment is then used as a speech token.

Alternatively, a library of tokens is provided, each token corresponding to a relatively short audio file. A large number of different types of audio files may be provided. The diversity between the files is used to explore how different MAPs process the files under common conditions. Each file is played in its entirety and can have predetermined lengths (e.g., four seconds). The library may include separate male and female sentence audio files. For example, the library could include 192 sentences from 64 different speakers (3 files per speaker) the speakers being male or female and having various accents or dialects. Preferably, each audio file incorporates a rich range of phenomenes and contextual cuing. In an alternative embodiment, long or short audio files within either a noise environment or from speech in babble (BKB) sentences is also used as tokens in addition to or in place of the tokens described above.

Referring now to FIG. 3C, the right side of the figure shows the 8 MAPs of a generation N. At block 352, the patient determines which 4 of the 8 MAPs are the clearest, in the sense that they are more preferred by the patient. In this manner, four of the MAPs are eliminated as indicated in FIG. 3C by the large X. The remaining MAPs are designated as MAPs A, B, C and D. These MAPs are used for reproduction as described herein.

Next, at block 354 a test is performed to determine if the algorithm should be stopped. In one embodiment, the algorithm is stopped after a predetermined number of generations. In another embodiment, the diversity of the surviving MAPs is compared to a threshold. If the diversity is below a limit (e.g., 0.1) then the surviving MAPs are the final MAPs that are processed as described herein. Otherwise the algorithm continues with reproduction.

As noted, reproduction comprises three steps: pairing, inheritance and mutation. Pairing occurs at block 356. As part of this operation, each surviving MAP forms pairs with some of the other surviving MAPs. In FIG. 3C, each MAP is paired with two other MAPs, forming four pairs are AB, BC CD and AD, as shown in FIG. 3C. Of course other pairs are possible as well.

The pairs of maps are used to generate two children or offspring at block 358. FIG. 3B shows how an offspring inherits some genes from each parent. For this purpose, a boundary or cutpoint is made in the bit string of each MAP. In FIG. 3C, this boundary is established at the middle of the bit string although it may be placed at other locations in alternative embodiments. In FIG. 3B, a child MAP 326 includes the first 4 bits of the Mother MAP 322 and the last 4 bits of the Father MAP 324.

Thus, at block 358, generation N+1 results from the pairings at block 356, using predetermined criteria. This process is further illustrated on the right side of FIG. 3C. The cut points govern inheritance of genes from each parent and are illustrated by the vertical dotted lines through each child on the right. Genes to the left of the cut point come from one parent, and genes to the right come from the other parent. In the illustrative example, the cut point is allowed to vary randomly across pairings. Alternatively, the cut points can be made in the same position for all the pairings.

As discussed above, in one embodiment, two children result from each pairing. The genes of each child may be selected from the genes of the parents in different ways. In one embodiment, the genes of one child include the genes from the left side of the cut in one parent and the genes from the right side of the cut from the other parent (as illustrated in FIGS. 2B and 2C). The genes for the other child are selected by copying the genes on the right side from the first parent and the left side from the second parent: Bits common to both parents are repeated.

More specifically, in FIG. 3C, each child is identified by a notation such as CD5. The first letter represents the organism in generation N that contributes leftmost bits to the child in generation N+1, the second letter represents the organism that contributes rightmost bits, and the numeral represents the position of the cuts. Lastly, as part of reproduction, a mutation is performed at block 360. Mutation is implemented by inverting some of the bits of at least some of the children in an arbitrary and random manner. For example, in FIG. 3C, the last or least significant bit in the sixth child of the new generation N+1 is inverted.

Once the new generation N+1 is formed, the fitness function is applied again at block 352 and the process continues.

The four final MAPs found at block 354 are checked further at block 362 to insure that their parameters are acceptable. In other words, a check can be performed to determine if the maps are valid, permissible, admissible or even realistic. If these final MAPs are not acceptable at block 362 then they are returned to the genetic algorithm. Alternatively, a different initial generation is selected at block 350 and the genetic algorithm is repeated. Alternatively, the operations at block 362 can be omitted.

If the final MAPs are found acceptable at block 364 then one of them is selected and used to program the cochlear implant system 100 at block 366 and stored at block 368. It has been found that after several iterations, the MAPs become very similar and, therefore, from a practical point of view, any one of the MAPs may be used. Alternatively, all the MAPs may be presented to the patient and the patient may be allowed to select the MAP that seems to perform best.

The 8 bits that represent a unique MAP give rise to 256 possible different bit strings that represent 256 unique MAPs. Several methods may be used to correlate each MAP to a corresponding set of parameters. Three such methods are discussed below.

FIG. 4 is a logical block diagram illustrating a manner in which a MAP formed of a bit string represents parameter values in accordance with one embodiment of the present invention. In this embodiment, 256 predetermined maps are chosen. Each MAP may represent any arbitrary admissible combination of parameters. For example, 256 different combinations thought to be useful by expert clinicians could be selected. The only constraint is that each combination be admissible and unique, that is, no two MAPs may represent the same combination of parameters. A lookup table associates each of the 256 possible bit strings with one of the 256 available MAPs. Therefore, when a bit string is specified, it uniquely represents a single MAP. With this method, each parameter can have any legal value in each MAP. For example, each of the 256 possible MAPs might have a different rate. In the embodiment illustrated in FIG. 4, five parameters are varied within the set of 256 MAPs.

In one exemplary embodiment, various, but not all, combinations of the following parameters are constructed within the set of 256 possible maps (some of the possible combinations are not valid clinically and are rejected): (1) Stimulation rate (one of 250, 720, 1200,1800, or 2400 Hz); (2) number of electrodes used (either 10 or 22); (3) number of maxima per stimulus frame (one of 4, 6, 8, 10, 12, 16, or 20); (4) steepness of output compression (known as the "Q" factor for an ACE or SPEAK map—either 20 or 30); and (5) combination of input audio filtering options (flat, high cut, low cut, or high and low cut). None of these parameters need to be individually represented by any particular subset or sub-string within the 8-bits.

Figure 5:
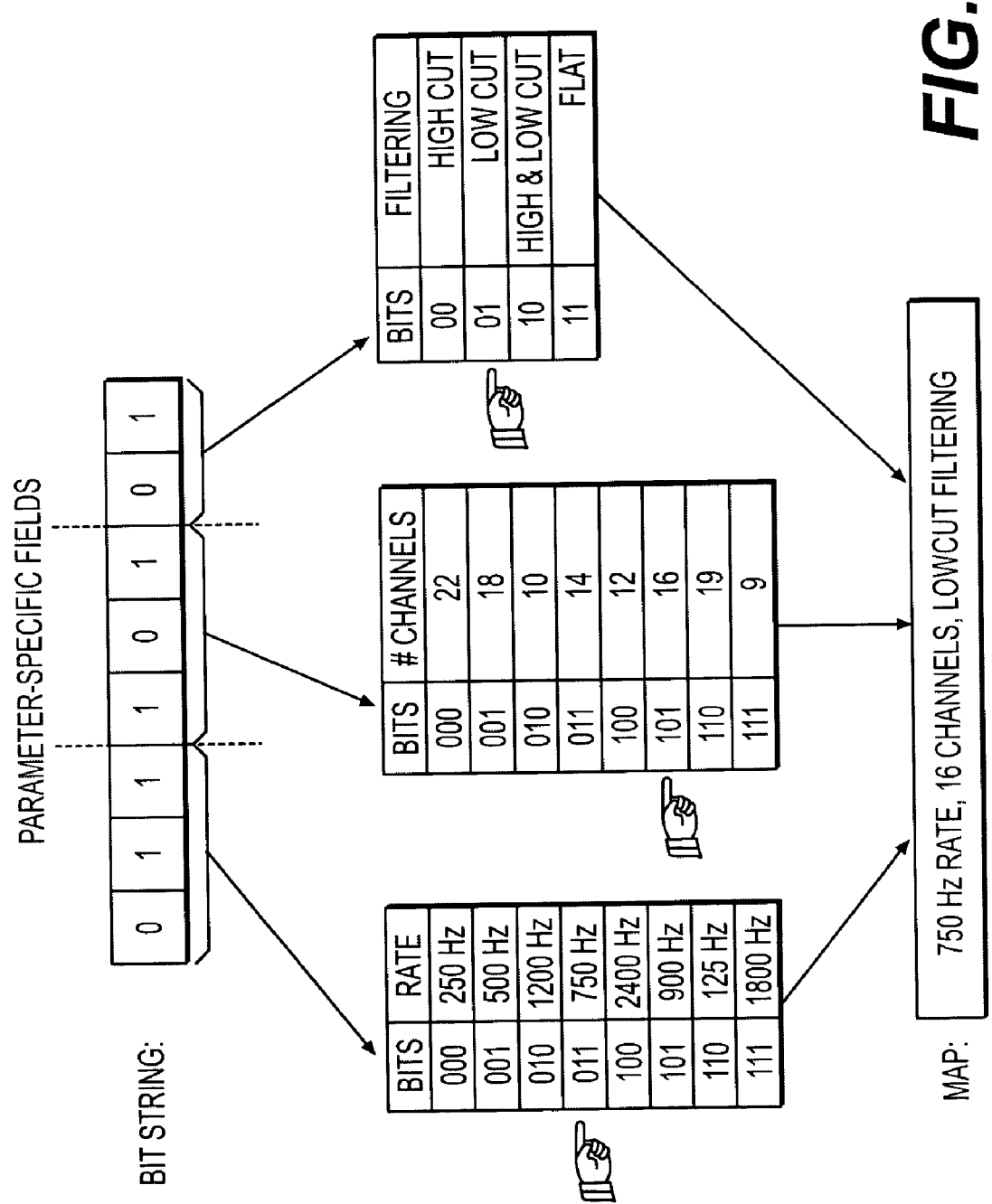
FIG. 5 is a logical block diagram illustrating a manner in which a parameter map formed of a bit string represents parameter values in accordance with one embodiment of the present invention.

FIG. 5 is a logical block diagram illustrating a manner in which a MAP formed of a bit string represents parameter values in accordance with one embodiment of the present invention. With this method, the bit string is broken down into sub-strings or fields. The sub-string in each field is then used to select a particular parameter for the MAP. In the example of FIG. 5, one 3-bit sub-string selects one of 8 possible rates for the MAP. A second 3-bit sub-string selects one of 8 possible channel counts, and a third 2-bit sub-string selects one of 4 possible filtering options. In this example, each sub-string is contiguous. However, this is not necessary, because there is no significance to the order of the bits in the bit string.

With this method, the available options for any given parameter are fixed by the number of bits in the corresponding sub-string. In the example of FIG. 5, only 8 different rates are available. No MAP can be defined with a rate of 792 Hz, for example, because this rate is not one of the 8 available alternatives.

Figure 6:
FIG. 6 is a logical block diagram illustrating a manner in which a parameter map formed of a bit string represents parameter values in accordance with one embodiment of the present invention.

FIG. 6 is a logical block diagram illustrating a manner in which a MAP formed of a bit string represents parameter values in accordance with one embodiment of the present invention. This method is a combination of the previous two methods. One or more sub-strings are defined to select corresponding parameters as in FIG. 5. The remaining bits are used to choose from a table of arbitrary combinations of the remaining parameters. In the example of FIG. 6, one 3-bit sub-string selects one of 8 possible rates. The remaining 5 bits are used to choose, from a lookup table, one of 32 arbitrary combinations of channel count and filtering. As with the first method, each of the 32 arbitrary combinations must be legal and unique.

FIG. 7 is a table of seven parameters that can be determined using the subject algorithm, and the possible values of each parameter, in accordance with one embodiment of the present invention. As previously discussed, the number of bits per MAP is not limited to 8. If more then 8 bits are used, the process can be used to optimize more parameters. In an alternate embodiment of the invention, 10-bit MAPs are used to optimize seven parameters: the five original parameters discussed above in conjunction with the 8-bit MAPs and two new parameters, FAT shift and T-level bump. These two parameters are described in more detail below. The seven parameters and their allowable values are shown in FIG. 7.

FIG. 8 is a table of a partial listing of 10-bit maps used to determine the parameters of FIG. 7, in accordance with one embodiment of the present invention. In FIG. 8, a listing of the first three binary MAPs used to determine the seven parameters of FIG. 7 and the respective parameter values, is shown. Some of these values are arbitrary numerical values. For example, a '1' for the FAT shift or the T-level bump designates the default value. '1', '2' and '3' for the filters designate the Low B, Low cut and high cut settings for the filters. Of course, the assignation of each set of parameter values to any 10-bit MAP is arbitrary.

It is well known in the art that a cochlear implant applies stimulation signals to 30 the aural nerves of a patient using a plurality of electrodes. The electrodes are grouped to define channels, each channel being used to apply signals corresponding to certain audible frequency bands. Typically, a cochlear system may use up to 23 channels and during the fitting of a cochlear implant a table is designated for the system that defines the number channels to be used and the frequency band allocated to each channel.

FIG. 9 is a table of a partial listing of frequency allocations to various channels to illustrate FAT shifting, in accordance with one embodiment of the present invention. Traditionally twenty seven tables are used to define up to 22 frequency bands corresponding to 22 channels. FIG. 9 is a partial listing of standardized frequency allocation tables (FATs) 6, 7, 8, 14, 15 and 16. Each table lists the upper frequency boundary of each band. The left column of FIG. 9 provides a frequency band index that identifies the rows of the listing. The rows of Table 6 indicates one possible frequency allocation for all frequency boundaries starting at 188 Hz for band 0 and ending with 7938 Hz for band 22. In fact, starting with table 6, the top frequency for the first channel is always allocated frequency 188 Hz and the top frequency for the last channel is always allocated 7938 Hz. Tables 1-5 have been omitted and contain slightly different frequency allocations to the 23 channels. Table 8 indicates the frequency allocation when 21 channels are used. Table 15 shows the frequency allocation for 14 channels. As can be seen from FIG. 9, as the number of utilized channels is reduced, the frequencies allocated to the highest channels are compressed. As a result of this compression, tables with lower number of channels provide a lower resolution of the audible signals at the high frequency ranges.

In the present invention, when the FAT shift parameter is set to its default value, the FAT tables of FIG. 9 are used. When the FAT shift is enabled, the tables are shifted to the left by a predetermined number of columns. In the preferred embodiment, FAT tables are shifted by one or two columns. For example, if table 8 is designated with 21 channels and the FAT shift is set at the default value then the frequency allocations shown in FIG. 9 for table 8 are used. If the FAT shift parameter is at a shift value, then the frequency values of the first 21 channels of table 6 are used. Thus for no shift, the channel 20 is designated the frequency 7938 Hz. When the shift parameter is 1, the channel 20 is designated 6063 Hz. For table 16, with no FAT shift, the channel 12 is designated the 7938 Hz frequency. With shift, table 15 is designated with channel 12 being allocated to 6313 Hz. The tradeoff is that the audible signals above the frequency allocated to channel 20 (for table 8) or channel 12 (for table 16) are lost.

Two other well-known programming parameters in cochlear systems are the T and C (threshold and comfort) levels. The T-level bump pertains to a feature of the invention wherein the T level is raised by a predetermined ratio (for example, 10-20% of the range between the original T and C levels). This feature improves the sensitivity of the system to soft sounds.

In addition, in the preferred embodiment, the filters parameter is augmented to include low B (low frequency boost), low C level and high C level. These parameter choices reduce the C level at low and high frequency, respectively.

Because not all combinations of parameter values are possible, only 1032 MAPs are required for the parameters shown in FIGS. 7 and 8. Since 10 bits can only define 1024 MAPs, eight combinations of parameter values are arbitrarily excluded.

A genetic algorithm has several properties that make it appealing for optimization of cochlear implant fitting. It is resistant to convergence upon local maxima, it is robust and can tolerate a noisy, inconsistent, or non-linear fitness function (e.g., subjective judgments by the user), it can incorporate 'expert knowledge,' and it is easily automated. Although less than all of the following can be specified in a practical application of the invention, a complete implementation for a cochlear map optimization may include one or more of the following: the choice of $N_b$; the method for defining a MAP from a set of $N_b$ bits (or, more generally, a set of genes); the number of MAPs per generation $N_g$; the method for defining the MAPs in the initial generation; the fitness function used to select survivors; the pairing operator used to determine the number of parental pairs per generation, and number of children per pair; the method for determining which of a child's genes come from each parent, that is, the cut point; the method for randomly determining which genes of a child are inverted from their inherited state; and stopping criterion.

Generally, all of these specifications are constant across generations, but this need not necessarily be the case. There may be specific advantages to having some of these specifications vary within a single evolutionary sequence.

The details of the implementation can significantly affect the behavior and efficiency of the algorithm, particularly its speed of convergence. The fitness function need not be purely subjective, e.g., it can be based on cortical evoked potentials either alone or with subjective inputs. But if the fitness function used involves subjective comparisons by a user, it is important to limit $N_g$ because a human listener cannot reasonably compare dozens of concurrent alternatives. A subjective fitness function is also 'expensive' in terms of time, which makes rapid convergence important. In general, the number of generations required for convergence rises with the number of genes per organism ($N_b$), so it is desirable to keep $N_b$ as small as possible while still representing those MAP parameters which are most likely to influence performance.

Preferably, at each iteration the user is given the opportunity to flag MAPs to be saved for future consideration. In this way if the process 'stumbles' onto a particularly good MAP it can be saved either at block 352 or at block 368 for comparison against the eventual result of the evolution. This eliminates the risk of frustrating the user. If multiple runs are used, saved designs, or designs resulting from a first run, can be included in the initial population for a subsequent run.

Expert knowledge can be incorporated into the process in various ways. As noted above, the MAPs of the initial generation can be based upon clinical judgment. Also specific parametric combinations known to be detrimental can be excluded from the universe of possible MAPs. Conversely, specific parametric combinations known to be beneficial can be condensed into a single 'parameter;' or occurrence of a specific value of one parameter may be used to override and dictate the value of a different parameter (e.g., any time the rate is >2400 Hz, the number of channels is limited to 10). Finally, as the population evolves, the expert may serve as an auxiliary form of input to guide the evolution in particular directions. For example, the clinician, based upon a visual representation of the evolution of the parameters, may anticipate more efficient paths to an optimal region. This expert knowledge can then be used to help steer the update mechanism in the proper direction.

The method of the invention has the advantage that it can be automated, requiring no supervision by the audiologist. It may also be repeated periodically as the recipient becomes more experienced. Separate optimizations may be performed for specific classes of input signals (e.g., speech in quiet, speech in noise, music, etc).

In some instances, it may be desirable to 'freeze' the values of one or more parameters after several iterations, using the value of the intermediate MAPs resulting from the iterations. For example, if at block 352 while analyzing the current generation of MAPs it is that all the survivors of a generation correspond to a subset of parameters that are identical (e.g., all the survivors have the same rate, the same number of maxima and the same number of electrodes), then these parameters are frozen. This may be accomplished in several ways. The simplest approach is to save the parameter values in a separate memory, let the algorithm run its course, and, at the end, when the final generation is obtained, substitute some of the 'final' parameters, that is, the parameters corresponding to the final MAPs with the 'frozen' parameters obtained during iterations.

Another approach is to use a different set of MAPs with lower bit series. For example, if originally 10-bit MAPs are used for eight parameters, and after some iterations, three of the parameter values are frozen, then a new set of 8-bit MAPs is used for the algorithm. The shorter MAPs used to continue the algorithm may consist of a set of initial MAPs as discussed above, or may be derived from the intermediate MAPs.

Finally, the algorithm itself may be modified so that after some of the parameters are frozen, portions of the MAPs are not changed anymore, i.e., they are not subject to gene selection. Of course, this approach is easiest to implement for MAP configurations in which all or some of bits of the MAPs correspond to, or represent specific parameter.

In principle, the recipient could perform optimizations at home using signals of his or her own choosing (e.g., a spouse's voice).

All documents, patents, journal articles and other materials cited in the present application are hereby incorporated by reference.

Although the present invention has been fully described in conjunction with several embodiments thereof with reference to the accompanying drawings, it is to be understood that various changes and modifications may be apparent to those skilled in the art. Such changes and modifications are to be understood as included within the scope of the present invention as defined by the appended claims, unless they depart therefrom.

What is claimed is:

1. A method for at least partially fitting a cochlear implant system to a patient comprising:
   executing a genetic algorithm to select values for a subset of one or more parameters selected from a plurality of parameters for which values are to be selected to fit said cochlear implant system, wherein said genetic algorithm is operable to generate one or more successive generations of values for said parameter subset; and
   determining, based on patient feedback, said values for said parameter subset in each of said one or more successive generations, wherein said patient feedback comprises a patient selection of at least one set of values for said parameter subset for use as a parent set in generating said successive generations; and
   programming the cochlear implant system using said selected values for the subset of one or more parameters.

2. The method of claim 1, wherein said one or more parameters interact non-linearly.

3. The method of claim 1, wherein said one or more parameters interact non-monotonically.

4. The method of claim 1, wherein said subset of one or more parameters comprises at least one of a group consisting of:
   a speech strategy implemented in said cochlear implant system;
   a quantity of channels represented in said cochlear implant system;
   which intracochlear and/or extracochlear electrodes are to be associated with each respective channel;
   a pulse repetition rate for each respective channel;
   a pulse width for each respective channel;
   a number of spectral maxima periodically chosen for representation;
   a mapping of sound pressure to stimulus current for each said respective channels;
   front end filtering of audio from a microphone;
   automatic gain control threshold;
   compression ratio; and
   attack and release times.

5. The method of claim 4, wherein said mapping of sound pressure to stimulus current for each channel comprises:
   one or more threshold levels;
   one or more comfort levels; and
   one or more compression curves.

6. The method of claim 1, wherein said cochlear implant system provides electrical and mechanical stimulation, and wherein said subset of at least one parameter comprises:
   at least one loudness parameter.

7. The method of claim 6, wherein said at least one loudness parameter comprises:
   one or more long term loudness balance parameters.

8. The method of claim 6, wherein said at least one loudness parameter comprises:
   one or more short term gain manipulations.

9. The method of claim 6, wherein said one or more short term gain manipulations comprises one or more signal-dependent gain adjustments.

10. The method of claim 9, wherein said one or more signal-dependent gain adjustments comprises one or more of a group consisting of:
    adjustments to minimize cross-modal masking; and
    adjustments to emphasize speech features.

11. The method of claim 10, wherein said speech features comprise one of frication and voicing.

12. The method of claim 1, wherein said cochlear implant system provides electrical and mechanical stimulation, and wherein said subset of at least one parameter comprises:
one or more frequency domain parameters.

13. The method of claim 12, wherein said one or more frequency domain parameters comprises:
frequency boundaries allocated to electrical and mechanical stimulation.

14. The method of claim 12, wherein said one or more frequency domain parameters comprises:
slopes of filtering at the boundaries of each stimulation signal.

15. The method of claim 12, wherein said one or more frequency domain parameters comprises:
allocation of frequency subbands in each domain.

16. The method of claim 1, wherein said cochlear implant system provides electrical and mechanical stimulation, and wherein said subset of at least one parameter comprises:
one or more time domain parameters.

17. The method of claim 16, wherein said one or more time domain parameters comprises:
adjusting electrical periodicity of pulse timing to be synchronized with mechanical signal fluctuations.

18. The method of claim 16, wherein said one or more time domain parameters comprises:
adjusting delays in electrical stimulus to compensate for missing propagation delays of various middle ear and inner ear pathways.

19. The method of claim 1, wherein said cochlear implant system provides electrical and mechanical stimulation, and wherein said subset of at least one parameter comprises:
one or more binaural parameters.

20. The method of claim 19, wherein said one or more binaural parameters comprises:
adjusting stimulus timing to present interaural timing cures.

21. The method of claim 19, wherein said one or more binaural parameters comprises:
adjustment of stimulus timing to suppress echo.

22. The method of claim 19, wherein said one or more binaural parameters comprises:
adjustment of stimulus timing to improve localization.

23. The method of claim 19, wherein said one or more binaural parameters comprises:
adjustment of stimulus timing to improve sound source segregation.

24. The method of claim 1, further comprising:
selecting values for parameters not included in said subset of at least one parameter by a method that does not use a genetic algorithm.

25. The method of claim 1, wherein said patient feedback comprises:
selecting, based on patient input, a specified quantity of values to survive in each generation from which said values for said parameter subset are determined for the next generation.

26. The method of claim 25, wherein values of said subset of parameters are represented by a string of bits.

27. The method of claim 26, wherein different sub-strings of bits in said string each represent values of respective parameters.

28. An apparatus for at least partially fitting a cochlear implant system to a patient comprising:
means for executing a genetic algorithm to select values for a subset of one or more parameters selected from a plurality of parameters for which values are to be selected to fit said cochlear implant system, wherein said genetic algorithm is operable to generate one or more successive generations of values for said parameter subset; and
means for determining, based on patient feedback, said values for said parameter subset in each of said one or more successive generations, wherein said patient feedback comprises a patient selection of at least one set of values for said parameter subset for use as a parent set in generating said successive generations.

29. The apparatus of claim 28, wherein said one or more parameters interact non-linearly.

30. The apparatus of claim 28, wherein said one or more parameters interact non-monotonically.

31. The apparatus of claim 28, wherein said subset of one or more parameters comprises at least one of a group consisting of:
a speech strategy implemented in said cochlear implant system;
a quantity of channels represented in said cochlear implant system;
which intracochlear and/or extracochlear electrodes are to be associated with each channel;
a pulse repetition rate for each channel;
a pulse width for each channel;
a number of spectral maxima periodically chosen for representation;
a mapping of sound pressure to stimulus current for each said channel;
front end filtering of the audio from the microphone;
automatic gain control threshold;
compression ratio; and
attack and release times.

32. The apparatus of claim 31, wherein said mapping of sound pressure to stimulus current for each channel comprises:
one or more threshold levels;
one or more comfort levels; and
one or more compression curves.

33. The apparatus of claim 28, wherein said cochlear implant system has means for providing electrical and mechanical stimulation, and wherein said subset of at least one parameter comprises:
at least one loudness parameter.

34. The apparatus of claim 33, wherein said at least one loudness parameter comprises:
one or more long term loudness balance parameters.

35. The apparatus of claim 33, wherein said at least one loudness parameter comprises:
one or more short term gain manipulations.

36. The apparatus of claim 35, wherein said one or more short term gain manipulations comprises:
one or more signal-dependent gain adjustments.

37. The apparatus of claim 36, wherein said one or more signal-dependent gain adjustments comprises one or more of a group consisting of:
adjustments to minimize cross-modal masking; and
adjustments to emphasize speech features.

38. The apparatus of claim 37, wherein said speech features comprise either frication or voicing.

39. The apparatus of claim 28, wherein said cochlear implant system has means for providing electrical and mechanical stimulation, and wherein said subset of at least one parameter comprises:
one or more frequency domain parameters.

40. The apparatus of claim 39, wherein said one or more frequency domain parameters comprises:
frequency boundaries allocated to electrical and mechanical stimulation.

41. The apparatus of claim 39, wherein said one or more frequency domain parameters comprises:
slopes of filtering at the boundaries of each stimulation signal.

42. The apparatus of claim 39, wherein said one or more frequency domain parameters comprises:
allocation of frequency subbands in each domain.

43. The apparatus of claim 28, wherein said cochlear implant system provides electrical and mechanical stimulation, and wherein said subset of at least one parameter comprises:
one or more time domain parameters.

44. The apparatus of claim 43, wherein said one or more time domain parameters comprises:
adjustment of electrical periodicity of pulse timing to be synchronized with mechanical signal fluctuations.

45. The apparatus of claim 43, wherein said one or more time domain parameters comprises:
adjustment of delays in the electrical stimulus to compensate for missing propagation delays of various middle ear and inner ear pathways.

46. The apparatus of claim 28, wherein said cochlear implant system provides electrical and mechanical stimulation, and wherein said subset of at least one parameter comprises:
one or more binaural parameters.

47. The apparatus of claim 46, wherein said one or more binaural parameters comprises:
adjustment of stimulus timing to present interaural timing cures.

48. The apparatus of claim 46, wherein said one or more binaural parameters comprises:
adjustment of stimulus timing to suppress echo.

49. The apparatus of claim 46, wherein said one or more binaural parameters comprises:
adjustment of stimulus timing to improve localization.

50. The apparatus of claim 46, wherein said one or more binaural parameters comprises:
adjustment of stimulus timing to improve sound source segregation.

51. The apparatus of claim 28, further comprising:
means for selecting values for parameters not included in said subset of at least one parameter by means that do not use a genetic algorithm.

52. The apparatus of claim 28, wherein said patient feedback comprises:
a specified quantity of values to survive in each generation from which said values for said parameter subset are determined for the next generation.

53. The apparatus of claim 52, wherein the values of said subset of parameters are represented by a string of bits.

54. The apparatus of claim 53, wherein different substrings of bits in said string each represent values of respective parameters.

55. A method for at least partially fitting a cochlear implant system to a patient comprising:
executing a genetic algorithm to select values for a subset of one or more parameters selected from a plurality of parameters for which values are to be selected to fit said cochlear implant system, wherein said genetic algorithm is operable to generate one or more successive generations of values for said parameter subset;
determining, based on patient feedback, said values for said parameter subset in each of said one or more successive generations, wherein said patient feedback comprises a patient selection of at least one set of values for said parameter subset for use as a parent set in generating said successive generations; and
programming the cochlear implant system using said selected values for the subset of one or more parameters, wherein said cochlear implant system is configured to provide both electrical and mechanical stimulation to the patient.

56. The method of claim 55, wherein said one or more parameters interact non-linearly.

57. The method of claim 55, wherein said one or more parameters interact non-monotonically.

58. The method of claim 55, wherein said subset of one or more parameters comprises:
a speech strategy implemented in said cochlear implant system.

59. The method of claim 55, wherein said subset of one or more parameters comprises:
a quantity of channels represented in said cochlear implant system.

60. The method of claim 55, wherein said subset of one or more parameters comprises:
which intracochlear and/or extracochlear electrodes are to be associated with each respective channel.

61. The method of claim 55, wherein said subset of one or more parameters comprises:
a pulse repetition rate for each respective channel.

62. The method of claim 55, wherein said subset of one or more parameters comprises:
a pulse width for each respective channel.

63. The method of claim 55, wherein said subset of one or more parameters comprises:
a number of spectral maxima periodically chosen for representation.

64. The method of claim 55, wherein said subset of one or more parameters comprises:
a mapping of sound pressure to stimulus current for each said respective channels.

65. The method of claim 55, wherein said subset of one or more parameters comprises:
front end filtering of audio from a microphone.

66. The method of claim 55, wherein said subset of one or more parameters comprises:
automatic gain control threshold.

67. The method of claim 55, wherein said subset of one or more parameters comprises:
compression ratio.

68. The method of claim 55, wherein said subset of one or more parameters comprises:
attack and release times.

69. The method of claim 55, wherein said mapping of sound pressure to stimulus current for each channel comprises:
one or more threshold levels;
one or more comfort levels; and
one or more compression curves.

70. The method of claim 55, wherein said subset of at least one parameter comprises:
at least one loudness parameter.

71. The method of claim 70, wherein said at least one loudness parameter comprises:
one or more long term loudness balance parameters.

72. The method of claim 70, wherein said at least one loudness parameter comprises:
one or more short term gain manipulations.

73. The method of claim 72, wherein said one or more short term gain manipulations comprises
one or more signal-dependent gain adjustments.

74. The method of claim 73, wherein said one or more signal-dependent gain adjustments comprises one or more of a group consisting of:
adjustments to minimize cross-modal masking; and
adjustments to emphasize speech features.

75. The method of claim 74, wherein said speech features comprise one of frication and voicing.

76. The method of claim 55, wherein said subset of at least one parameter comprises:
one or more frequency domain parameters.

77. The method of claim 76, wherein said one or more frequency domain parameters comprises:
frequency boundaries allocated to electrical and mechanical stimulation.

78. The method of claim 76, wherein said one or more frequency domain parameters comprises:
slopes of filtering at the boundaries of each stimulation signal.

79. The method of claim 76, wherein said one or more frequency domain parameters comprises:
allocation of frequency subbands in each domain.

80. The method of claim 55, wherein said subset of at least one parameter comprises:
one or more time domain parameters.

81. The method of claim 80, wherein said one or more time domain parameters comprises:
adjusting electrical periodicity of pulse timing to be synchronized with mechanical signal fluctuations.

82. The method of claim 80, wherein said one or more time domain parameters comprises:
adjusting delays in electrical stimulus to compensate for missing propagation delays of various middle ear and inner ear pathways.

83. The method of claim 55, wherein said subset of at least one parameter comprises:
one or more binaural parameters.

84. The method of claim 83, wherein said one or more binaural parameters comprises:
adjusting stimulus timing to present interaural timing cures.

85. The method of claim 83, wherein said one or more binaural parameters comprises:
adjustment of stimulus timing to suppress echo.

86. The method of claim 83, wherein said one or more binaural parameters comprises:
adjustment of stimulus timing to improve localization.

87. The method of claim 83, wherein said one or more binaural parameters comprises:
adjustment of stimulus timing to improve sound source segregation.

88. The method of claim 55, further comprising:
selecting values for parameters not included in said subset of at least one parameter by a method that does not use a genetic algorithm.

89. The method of claim 55, wherein said patient feedback comprises:
selecting, based on patient input, a specified quantity of values to survive in each generation from which said values for said parameter subset are determined for the next generation.

90. The method of claim 89, wherein values of said subset of parameters are represented by a string of bits.

91. The method of claim 90, wherein different sub-strings of bits in said string each represent values of respective parameters.

92. A method of at least partially fitting a medical implant system to a patient comprising:
executing a genetic algorithm to select values for one or more parameters selected from a plurality of parameters for which values are to be generated to fit said medical implant system, wherein said genetic algorithm is operable to generate one or more successive generations of values for said selected parameters;
selecting, based on patient feedback, values for a smaller portion of said selected parameters and determining from said values of said smaller portion a larger number of parameter values for the next generation of values; and
programming the medical implant system using said selected values for the subset of one or more parameters.

93. A method of at least partially fitting a medical implant system to a patient comprising:
forming a plurality of sequences of one or more digits having digit groups which represent parameter values for the implant;
receiving patient feedback from testing said parameter values, specifying which of said formed digit sequences provide superior performance and are to be used as a parent sequence;
combining one or more digits of said parent sequences to form new digit sequences; and
iteratively repeating said selecting and said combining steps to determine a sequence for use in fitting said medical implant system; and
programming the medical implant system using said values corresponding to the determined sequence.

94. A method of at least partially fitting a medical implant system to a patient comprising:
selecting one or more parameters from a plurality of parameters for which values are to be generated to fit said medical implant system;
generating one or more successive generations of values for said selected comprising:
receiving patient feedback specifying a at least one set of parameter values for use in determining a next generation of parameter values; and
determining, from the specified set of parameter values, parameters values for the next generation of parameter values; and
programming the medical implant system using said selected values for the subset of one or more parameters.

95. The method of claim 93, wherein said medical implant system provides electrical and mechanical stimulation to the patient.

96. The method of claim 93, wherein said medical implant system is a binaural system.

97. The method of claim 93, further comprising:
selecting values for parameters used to fit said medical implant system by a method that does not use a genetic algorithm.

98. The method of claim 94, wherein said medical implant system provides electrical and mechanical stimulation to the patient.

99. The method of claim 94, wherein said medical implant system is a binaural system.

100. The method of claim 94, further comprising:

selecting values for parameters used to fit said medical implant system by a method that does not use a genetic algorithm.

* * * * *